United States Patent
Bugher et al.

(10) Patent No.: US 9,863,866 B2
(45) Date of Patent: Jan. 9, 2018

(54) BI-DIRECTIONAL AIR-CURTAIN FOR COLD TESTING A CAMERA

(71) Applicant: Delphi Technologies, Inc., Troy, MI (US)

(72) Inventors: Robert R. Bugher, Russiaville, IN (US); Scott E. Stoerger, Kokomo, IN (US); James C. Baar, Logansport, IN (US)

(73) Assignee: DELPHI TECHNOLOGIES, INC., Troy, MI (US)

( * ) Notice: Subject to any disclaimer, the term of this patent is extended or adjusted under 35 U.S.C. 154(b) by 150 days.

(21) Appl. No.: 14/967,819

(22) Filed: Dec. 14, 2015

(65) Prior Publication Data

US 2017/0167967 A1   Jun. 15, 2017

(51) Int. Cl.
*G01N 17/00* (2006.01)

(52) U.S. Cl.
CPC .................. *G01N 17/002* (2013.01)

(58) Field of Classification Search
None
See application file for complete search history.

(56) References Cited

U.S. PATENT DOCUMENTS

| | | | |
|---|---|---|---|
| 5,341,676 A * | 8/1994 | Gouterman | G01M 9/06 250/459.1 |
| 6,543,078 B1 * | 4/2003 | Ernst | B08B 6/00 15/1.51 |
| 6,554,210 B2 * | 4/2003 | Holt | B05B 7/08 239/284.1 |
| 6,902,630 B2 * | 6/2005 | Ernst | B08B 6/00 134/1 |
| 7,181,985 B2 * | 2/2007 | MacMillan | F16L 55/30 73/865.8 |
| 8,776,722 B2 * | 7/2014 | Andersson | A01J 5/0175 119/14.02 |
| 2010/0013984 A1 * | 1/2010 | Loiacono | G03B 17/08 348/373 |
| 2013/0247827 A1 * | 9/2013 | Andersson | A01J 5/0175 119/14.02 |
| 2014/0104426 A1 * | 4/2014 | Boegel | B60R 1/00 348/148 |
| 2015/0216402 A1 * | 8/2015 | Ray | A61B 1/126 600/109 |
| 2016/0311405 A1 * | 10/2016 | Richardson | G02B 27/0006 |

* cited by examiner

*Primary Examiner* — Lisa Caputo
*Assistant Examiner* — Tran M Tran
(74) *Attorney, Agent, or Firm* — Lawrence D. Hazelton

(57) ABSTRACT

A cold-test system for testing a camera at a cold temperature includes a test-chamber with a window, a nozzle, and a recirculator. The window is installed in the test-chamber so the camera is provided with a view of a test-target outside of the test-chamber. The nozzle is located proximate to a first edge of the window. The nozzle is configured to direct air from an air-source in a first direction and adjacent to an outside-surface of the window. The recirculator is located proximate to a second edge of the window opposite the first edge. The recirculator is configured to receive the air moving in the first direction and re-direct that air in a second direction opposite the first direction and adjacent to the air moving in the first direction opposite the window. The nozzle and the recirculator cooperate to form a bi-directional air-curtain proximate to the outside-surface.

9 Claims, 2 Drawing Sheets

BI-DIRECTIONAL AIR-CURTAIN FOR COLD TESTING A CAMERA

TECHNICAL FIELD OF INVENTION

This disclosure generally relates to a cold-test system for a camera, and more particularly relates to forming a bi-directional air-curtain to prevent condensation on a window of an environmental test chamber through which the camera views a test target.

BACKGROUND OF INVENTION

It is desired to test the operation and performance of a camera at temperatures other than ambient, e.g. cold temperatures such as −40° C. Cold testing is typically done inside an environmental test-chamber. However, the targets used to determine the operation and performance of a camera may be too large to fit inside an economically priced test-chamber. It has been suggested to place the target outside of the test-chamber and have the camera view the target through the multi-pane viewing-window that is typically provided with a test-chamber. The viewing-window is a multi-pane configuration to prevent fogging/frosting of the viewing window during cold testing. However, the multi-pane configuration causes an unacceptable amount of image distortion for camera testing.

SUMMARY OF THE INVENTION

In accordance with one embodiment, a cold-test system for testing a camera at a cold temperature is provided. The system includes a test-chamber with a window, a nozzle, and a recirculator. The test-chamber is configured to establish a cold temperature for testing a camera therein. The window is installed in the test-chamber so the camera is provided with a view of a test-target outside of the test-chamber. The nozzle is located proximate to a first edge of the window. The nozzle is configured to direct air from an air-source in a first direction and adjacent to an outside-surface of the window. The outside-surface is characterized as outside the test-chamber. The recirculator is located proximate to a second edge of the window opposite the first edge. The recirculator is configured to receive the air moving in the first direction and re-direct that air in a second direction opposite the first direction and adjacent to the air moving in the first direction opposite the window.

In another embodiment, an apparatus to maintain a surface-temperature of an outside-surface of a window of a test-chamber greater than a dew-point temperature is provided. The apparatus includes a nozzle and a recirculator. The nozzle is located proximate to a first edge of a window of a test-chamber. The nozzle is configured to direct air from an air-source in a first direction and adjacent to an outside-surface of the window outside the test-chamber. The recirculator is located proximate to a second edge of the window opposite the first edge. The recirculator is configured to receive the air moving in the first direction and re-direct that air in a second direction opposite the first direction and adjacent to the air moving in the first direction opposite the window.

Further features and advantages will appear more clearly on a reading of the following detailed description of the preferred embodiment, which is given by way of non-limiting example only and with reference to the accompanying drawings.

BRIEF DESCRIPTION OF DRAWINGS

The present invention will now be described, by way of example with reference to the accompanying drawings, in which.

DETAILED DESCRIPTION

Figure 1:
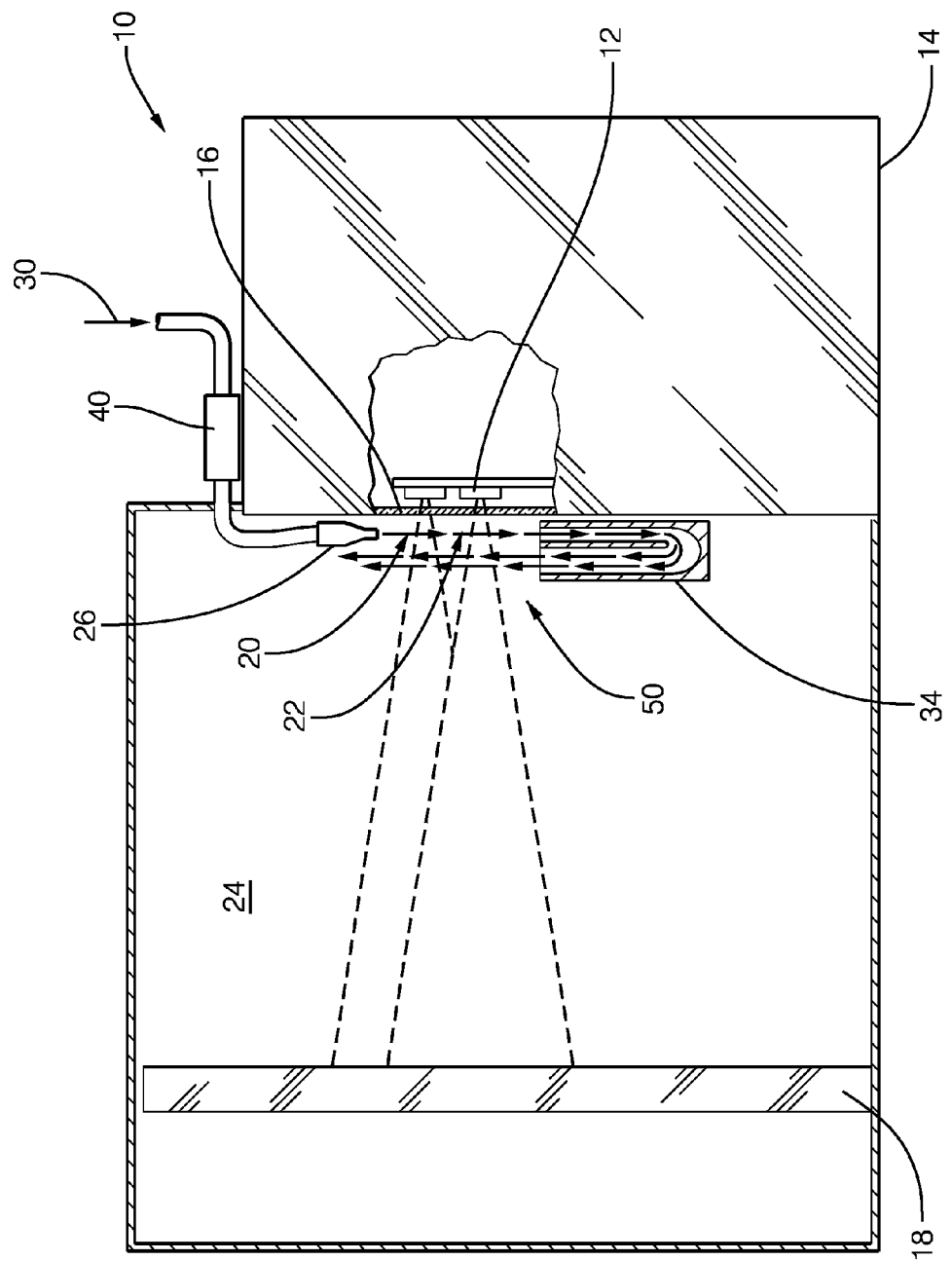
FIG. 1 is cold-test system for testing a camera at a cold temperature in accordance with one embodiment.
Figure 2:
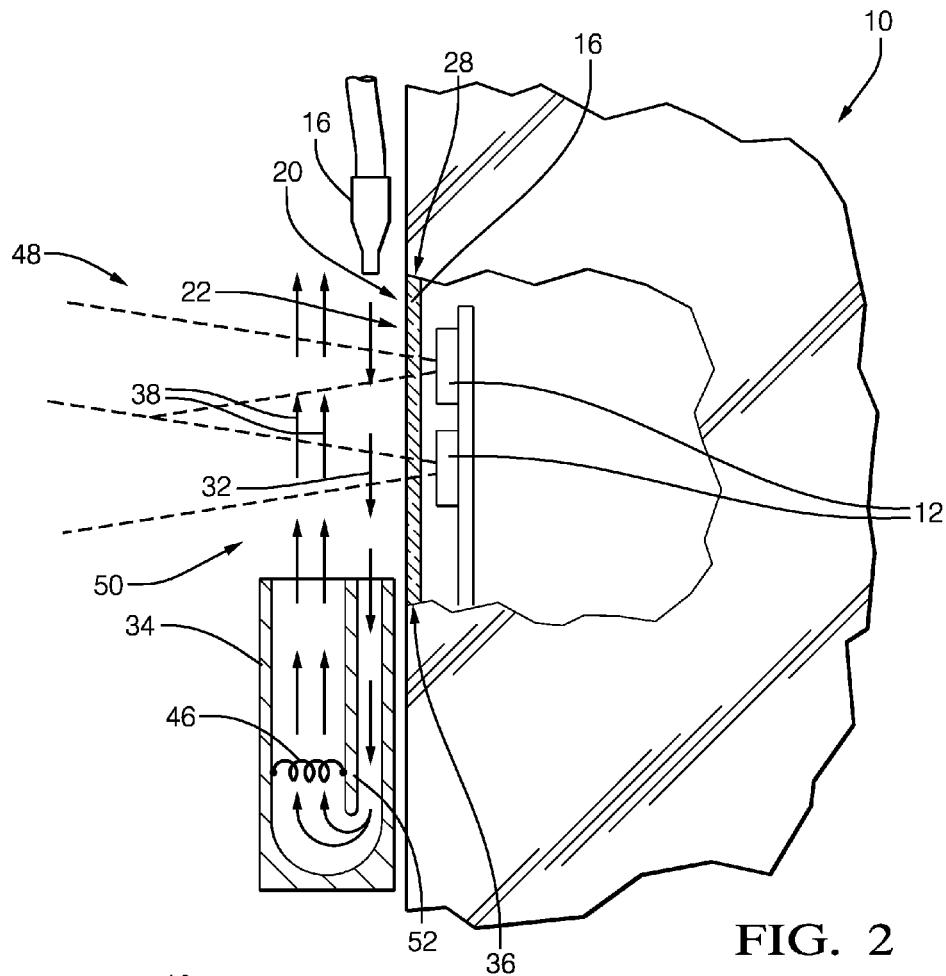
FIG. 2 is a close-up view of part of the system of FIG. 1 in accordance with one embodiment.

FIGS. 1 and 2 illustrate a non-limiting example of a system 10 for testing a camera 12 or multiple instances of the camera 12. While the system 10 may be suitably configured to test the camera 12 at a variety of temperatures (increased or decreased relative to ambient temperature), improvements presented herein are directed to problems that may arise while testing cameras at relatively cold temperatures. The system 10 includes a test-chamber 14 configured to establish a cold temperature (e.g. −40° C.) for testing the camera 12 within the test-chamber 14. A window 16 is installed in a wall or door of the test-chamber 14 so the camera 12 is provided with a view of a test-target 18 outside the confines of the test-chamber 14.

The window 16 preferable consists of a single-layer of transparent material rather than multiple layers which could distort the image of the test-target 18 captured or taken by the camera 12. By way of example and not limitation, the window 16 may advantageously formed of a single pane of borosilicate glass such as BOROFLOAT® 33 manufactured by SCHOTT Technical Glass Solutions GmbH, which has been shown to be useful at anticipated test temperatures, and provides for adequate clarity for testing the camera 12. However, at cold test temperatures condensation and/or frosting of an outside-surface 20 of the window 16 has been observed when a surface-temperature 22 of the outside-surface 20 is less than a dew-point temperature 24 of the air in contact with the outside-surface 20.

To address this problem, the system 10 includes a nozzle 26 located proximate to a first edge 28 of the window 16. In general, the nozzle 26 is configured to direct air from an air-source 30 in a first direction 32 and adjacent to, i.e. across and in contact with, the outside-surface 20 of the window 16 outside the test-chamber 14. The air-source 30 preferable provides dried air, at least dryer than the air proximate the test-target 18 which is characterized by the dew-point temperature 24. As will become evident with further description, air, preferably dry air, from the nozzle 26 is used to remove or prevent condensation and/or frosting of the outside-surface 20 so the camera 12 has a clear, undistorted view of the test-target 18 through the window 16. By way of example and not limitation, the nozzle 26 may be an AIRWISK® nozzle manufactured by BEX Incorporated. While 'nozzle' is used in singular form, it is contemplated that a plurality of nozzles may be necessary to keep the entire window free from condensation and/or frosting.

The system 10 also advantageously includes a recirculator 34 located proximate to a second edge 36 of the window 16 opposite the first edge 28. The recirculator 34 is generally configured to receive the air moving in the first direction 32 and re-direct that air in a second direction 38 opposite the first direction 32. The recirculator 34 is also advantageously configured so air moving in the second direction 38 is adjacent to (i.e. close to and/or next to) the air moving in the first direction 32. This arrangement locates the air moving in the second direction 38 adjacent to the air moving in the first direction 32 and opposite the outside-surface 20 the window 16. The air flowing in the first direction 32 is directed or aimed to 'contact' the outside-surface 20. The air flowing in the second direction 38 is directed to 'contact' or be as close as possible to the air flowing in the first direction 32 without undesirable disruption of the air flowing in the first direction 32. That is, air flowing in the first direction 32 is 'sandwiched' between the outside-surface 20 and the air flowing in the second direction 38. The cooperation of adjacent air streams flowing in opposite directions creates what can be described as a bi-directional air-curtain 50, which is intended to keep moisture present in the ambient air outside of the test-chamber 14 from condensing on the outside-surface.

While dried room-temperature (e.g. 23° C.) air blown across the window 16 from the nozzle 26 may be sufficient to keep the surface-temperature 22 greater than the dew-point temperature 24, heating of that air may be necessary when the chamber temperature is extremely low and/or the dew-point temperature is relatively high. As such, the system 10 may include a source-heater 40 operable to provide heat 42 (FIG. 3) to the air from the air-source 30 that is emitted by the nozzle 26. The source-heater 40 may include a resistive-heating element 44 (FIG. 3), or may be a combustible fuel (e.g. natural gas) type heater. Similarly, the recirculator 34 may be equipped with a recirculator-heater 46 operable to heat air passing through the recirculator 34. The recirculator-heater 46 may be electrically or chemically powered and may be provided in addition or as an alternative to the source-heater 40. While various parts that cooperate to keep the window 16 free from condensation have been described as part of the system 10, it is contemplated that the nozzle 26 and the recirculator 34 may be sold separately as a kit or apparatus 48 to maintain the surface-temperature 22 of the outside-surface 20 of the window 16 of a test-chamber 14 greater than the dew-point temperature 24 of ambient air outside of the text-chamber 14.

To help manage the flow of air within the recirculator 34, a divider 52 may be provided so air traveling in the first direction 32 can be predictably re-routed into the second direction 38 and past the recirculator-heater 46 if so equipped. The shape and location of the divider 52 maybe selected based on expected air-flow rates and/or acoustic noise requirements.

Figure 3:
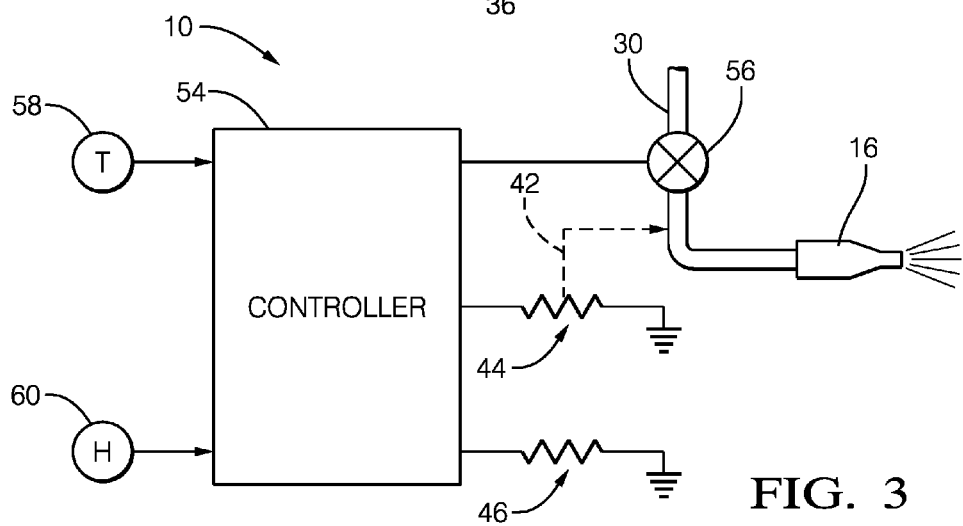
FIG. 3 is schematic diagram of the system of FIG. 1 in accordance with one embodiment.

FIG. 3 illustrates further non-limiting details of the system 10. Electrical power or other control signals may be provided to the resistive-heating element 44 and the recirculator-heater 46 by a controller 54. The controller 54 may include a processor such as a microprocessor or other control circuitry such as analog and/or digital control circuitry including an application specific integrated circuit (ASIC) for processing data as should be evident to those in the art. The controller 54 may include memory, including non-volatile memory, such as electrically erasable programmable read-only memory (EEPROM) for storing one or more routines, thresholds, and captured data. The one or more routines may be executed by the processor to perform steps for determining if signals received by the controller 54 suggest the presence or possibility of condensation on the outside-surface 20.

Continuing to refer to FIG. 3, the system 10 may include a valve 56 operable by the controller 54 to vary the amount of air being emitted by the nozzle 26. The system may also include one or more instances of a temperature sensor 58 and/or a humidity sensor 60 so the controller can determine the dew-point temperature 24, the surface-temperature 22, and/or detect condensation on the outside-surface 20.

Accordingly, a cold-test system 10 for testing a camera at a cold temperature, a controller 54 for the system 10 and an apparatus 48 to maintain a surface-temperature of an outside-surface of a window of a test-chamber greater than a dew-point temperature is provided. The addition of the recirculator 34 substantially improves the ability of the system 10 or apparatus 48 to keep the outside-surface 20 free from condensation and/or frost because the barrier of relatively warm and/or dry air created by the bi-directional air-curtain 50 performs better than prior attempts that only have a single-direction air-curtain.

While this invention has been described in terms of the preferred embodiments thereof, it is not intended to be so limited, but rather only to the extent set forth in the claims that follow.

We claim:

1. A cold-test system for testing a camera at a cold temperature, said system comprising:
   a test-chamber configured to establish a cold temperature for testing a camera therein;
   a window installed in the test-chamber so the camera is provided with a view of a test-target outside of the test-chamber;
   a nozzle located proximate to a first edge of the window, said nozzle configured to direct air from an air-source in a first direction parallel to an outside-surface of the window, said outside-surface characterized as outside the test-chamber; and
   a recirculator located proximate to a second edge of the window opposite the first edge, said recirculator configured to receive the air from the nozzle moving in the first direction and re-direct that same air in a second direction opposite the first direction and adjacent to the air moving in the first direction opposite the window.

2. The system in accordance with claim 1, wherein the nozzle and the recirculator cooperate to form a bi-directional air-curtain proximate to the outside-surface.

3. The system in accordance with claim 1, wherein the window is characterized as consisting of a single-layer of transparent material.

4. The system in accordance with claim 1, wherein the system includes a source-heater operable to heat air from the air-source that is emitted by the nozzle.

5. The system in accordance with claim 1, wherein the system includes a recirculator-heater operable to heat air passing through the recirculator.

6. An apparatus to maintain a surface-temperature of an outside-surface of a window of a test-chamber greater than a dew-point temperature, said apparatus comprising:
   a nozzle located proximate to a first edge of the window, said nozzle configured to direct air from an air-source in a first direction parallel to an outside-surface of the window, said outside-surface characterized as outside a test-chamber; and
   a recirculator located proximate to a second edge of the window opposite the first edge, said recirculator configured to receive the air from the nozzle moving in the first direction and re-direct that same air in a second direction opposite the first direction and adjacent to the air moving in the first direction opposite the window.

7. The apparatus in accordance with claim 6, wherein the nozzle and the recirculator cooperate to form a bi-directional air-curtain proximate to the outside-surface.

8. The apparatus in accordance with claim 6, wherein the apparatus includes a source-heater operable to heat air from the air-source that is emitted by the nozzle.

9. The apparatus in accordance with claim 6, wherein the apparatus includes a recirculator-heater operable to heat air passing through the recirculator.

\* \* \* \* \*